United States Patent [19]

Boyer et al.

[11] Patent Number: 5,662,902
[45] Date of Patent: Sep. 2, 1997

[54] COMPOSITIONS FOR THE PREVENTION AND TREATMENT OF VIRAL-INDUCED TUMORS

[75] Inventors: Ernest W. Boyer; Robert L. Charles, both of Elkhart, Ind.

[73] Assignee: Genencor International, Inc., Rochester, N.Y.

[21] Appl. No.: 463,363

[22] Filed: Jun. 5, 1995

Related U.S. Application Data

[62] Division of Ser. No. 126,660, Sep. 27, 1993, Pat. No. 5,500,359.
[51] Int. Cl.$^6$ .............................. A61K 35/70; C12N 1/14
[52] U.S. Cl. .................. 424/115; 435/256.1; 435/917; 514/886; 514/887
[58] Field of Search .................. 424/115; 435/256.1, 435/917; 514/886, 887

[56] References Cited

U.S. PATENT DOCUMENTS

| | | | |
|---|---|---|---|
| 3,230,153 | 1/1966 | Olson et al. | 435/171 |
| 3,819,832 | 6/1974 | Joshi | 424/115 |
| 3,930,955 | 1/1976 | Kusakabe et al. | 435/227 |
| 5,073,630 | 12/1991 | Nunes et al. | 530/400 |

FOREIGN PATENT DOCUMENTS

| | | |
|---|---|---|
| 0143403 | 6/1985 | European Pat. Off. . |
| 57-7420 | 4/1982 | Japan . |
| 57-95913 | 9/1982 | Japan . |
| 0311021 | 4/1991 | Japan . |
| 9400303 | 11/1994 | WIPO . |

OTHER PUBLICATIONS

Takeshima, H., Chapter 3: The Search for Bioactive Compounds from Microorganisms, Omura, S., ed., pp. 45-62, Springer-Verlag, New York, Inc. (1992).

Lewis, R., "Interferon Must Prove Itself In Market for Genital Warts," *Genetic Engineering News*, vol. 15, No. 5 (1995).

R. A. Fisher, Statistical Methods for Research Workers, 14th Edition Hafner, N.Y., N.Y. (1973).

B. E. Korba et al., Antiviral Research, vol. 19, pp. 55-70 (1992).

K. W. King et al., Applied Microbiology, vol. 11, pp. 315-319 (1963).

L. H. Li et al., Applied Microbiology, vol. 11, pp. 320-325 (1963).

B. Lidin et al., Antiviral Research, vol. 17, pp. 79-89 (1992).

D. J. Finney, Biometrika, vol. 35, pp. 145-156 (1948).

R. Latscha, Biometrika, vol. 40, pp. 74-86 (1955).

S. Dowdy et al., Chi Square Distributions In: Statistics for Research, pp. 97-124 J. Wiley & Sons, Inc., N.Y., N.Y. (1983).

N. J. Poindexter et al., The Journal of Infectious Diseases, vol. 151, No. 1, pp. 65-72 (1985).

R. S. Ostrow et al., Virology, vol. 108, pp. 21-27 (1981).

D. A. Manias et al., Cancer Research, vol. 49, pp. 2514-25198 (1989).

R. S. Ostrow et al., Proc. Natl. Acad. Sci. USA., vol. 79, pp. 1634-1638 (1982).

R. S. Ostrow, Antiviral Research, vol. 17, pp. 99-133 (1992).

S. L. Watts et al., Virology, vol. 125, pp. 127-138 (1983).

*Primary Examiner*—John W. Rollins
*Assistant Examiner*—Francisco C. Prats

[57] ABSTRACT

Prophylactic and therapeutic agents for the prevention and treatment of viral-induced tumors and, in particular, compositions derived from an Aspergillus fermentation extract, and the use thereof, either directly or to prepare a medicament, for the prevention and treatment of viral-induced tumors in mammals. Such tumors include papilloma-induced tumors. The composition is topically administered.

3 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAACTGCCTG CCACGCTCGC         20

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCCTGGCCC TAGGTCAAC         19

COMPOSITIONS FOR THE PREVENTION AND TREATMENT OF VIRAL-INDUCED TUMORS

This is a divisional of application Ser. No. 08/126,660 filed Sep. 27, 1993 now U.S. Pat. No. 5,500,359.

FIELD OF THE INVENTION

The present invention relates to prophylactic and therapeutic agents for the prevention and treatment of viral-induced tumors and, in particular, to compositions derived from Aspergillus fermentation extracts for use as a topical agent for the prevention and treatment of viral-induced tumors, such as papillomavirus-induced tumors, in mammals.

BACKGROUND OF THE INVENTION

Viruses which induce tumors in mammals are quite widespread. Indeed, there are over sixty-eight types of human papillomaviruses (HPV) alone which can induce the production of tumors. Some of these HPV's have been associated with benign tumors, such as common warts, while others have been strongly implicated as etiologic agents in dysplasia and carcinomas in the oral and genital mucosa of the infected mammal. Other types of viruses which can result in tumors include various RNA viruses as well as herpes viruses.

Recently, it has also been observed that individuals with depressed immune systems, such as sufferers of Aquired Immune Deficiency Syndrome (AIDS), are prone to human papillomavirus infections which can result in tumor growth over their entire bodies, resulting in great mental and physical distress to the afflicted individual.

Current modalities for the treatment of viral-induced tumors involve the removal of the tumor by either: (1) surgical intervention (laser or operative); (2) the application of organic acids, such as glacial acetic acid and/or salicyclic acid, to "burn" the tumor away; (3) the injection into the tumor of an anti-tumor vaccine prepared from ground tumors; and, to a lesser extent, (4) the application of a drug treatment (such as podophyllin, 5-FU and interferons).

While being useful for removing the viral-induced tumor, the current treatment modalities presently used nonetheless suffer from one or more of the following drawbacks: (1) they can result in the destruction of healthy uninfected tissue; (2) they can result in scarring and disfigurement; (3) they can result in discomfort to the mammal being treated thereby; and (4) they do not always result in the destruction of latent viral DNA which may be maintained in surrounding tissues. Furthermore, with these treatments, patients have suffered from significant systemic side effects, incomplete resolution and frequent recurrences of the tumors.

It has also been disclosed to use phototherapy for removing laryngeal papillomatosis tumors. While such phototherapy reduced tumor growth by about 50%, it also resulted in a generalized skin photosensitivity for at least six weeks, as well as other minor reactions. Furthermore, despite the apparent success of this technique, the presence of latent viral DNA is nonetheless still maintained in the surrounding tissues.

U.S. Pat. No. 5,073,630 discloses a polymeric anhydride of magnesium and proteic ammonium phospholinoleate with antiviral, antineoplastic and immunostimulant properties. This antiviral agent was produced in the cell-free filtrate of a selected line of Aspergillus sp. However, that compound is insoluble in water and possesses a high molecular weight (316,000 daltons).

Accordingly, it can be seen that there remains a need for prophylactic and therapeutic compositions capable of preventing and treating viral-induced tumors in mammals without either destroying healthy uninfected tissue, causing significant systemic side effects, causing scarring or disfigurement of, and/or discomfort to, the mammal treated therewith, and which results in the destruction of latent viral DNA which may be maintained in surrounding tissues, so that instances of incomplete resolution and frequent recurrences of the tumors are reduced. It can further be seen that there also remains a need for methods for providing such prophylactic and therapeutic compositions, as well as methods for the use of such a prophylactic and therapeutic compositions for the prevention and treatment of viral-induced tumors in mammals.

SUMMARY OF THE INVENTION

It is a primary object of the present invention to provide prophylactic and therapeutic compositions for the prevention and treatment of viral-induced tumors in mammals which compositions neither destroy healthy uninfected tissue, nor result in either significant systemic side effects, scarring, disfigurement or discomfort to the mammal treated therewith, and further which result in the destruction of latent viral DNA which may be maintained in surrounding tissues, so that instances of incomplete resolution and frequent tumor recurrence are reduced.

It is a further primary object of the present invention to provide simple, easy to perform methods for providing such prophylactic and therapeutic compositions for the prevention and treatment of viral-induced tumors in mammals.

It is a still further primary object of the present invention to provide methods for preventing and treating viral-induced tumors in mammals which methods neither destroy healthy uninfected tissue, nor result in either significant systemic side effects, scarring, disfigurement or discomfort to the mammal treated therewith, and further which result in the destruction of latent viral DNA which may be maintained in surrounding tissues, so that instances of incomplete resolution and frequent tumor recurrence are reduced.

In accordance with the teachings of the present invention, disclosed herein are prophylactic and therapeutic compositions for the prevention and treatment of viral-induced tumors in mammals. These compositions neither destroy healthy uninfected tissue, nor result in either significant systemic side effects, scarring, disfigurement or discomfort to the mammal treated therewith. Furthermore, these compositions result in the destruction of latent viral DNA maintained in surrounding tissues, so that instances of incomplete resolution and frequent tumor recurrence are reduced.

It is preferred that these prophylactic and therapeutic compositions be suitable for topical uses.

Preferably, the prophylactic and therapeutic compositions of the present invention are fermentation extracts and/or derivatives thereof. It is further preferred that these fermentation extracts be an Aspergillus fermentation extract. A preferred Aspergillus fermentation extract is an *Aspergillus niger* fermentation extract with *Aspergillus niger* 1.2 AN29 and *Aspergillus niger* 1.2 AN39 fermentation extracts being especially preferred.

It is still further preferred that the compositions of the present invention include these fermentation extracts and/or derivatives thereof in a pharmaceutically-acceptable carrier.

In a preferred embodiment, the compositions of the present invention include concentrated fermentation extracts.

If desired, the compositions of the present invention may be enzyme compositions which are either derivatives of and/or have been derived from the fermentation extract(s) disclosed herein.

In a particular aspect of the present invention, the Aspergillus fermentation extracts (and/or derivatives thereof) described herein are used for the preparation of prophylactic and therapeutic compositions for the prevention and treatment of viral-induced tumors in mammals. Preferably, the Aspergillus fermentation extracts (and/or derivatives thereof) are used for the preparation of such prophylactic and therapeutic compositions which may be topically applied to a mammal in need thereof.

In further accordance with the teachings of the present invention, disclosed herein are methods for providing the prophylactic and therapeutic compositions of the present invention. These methods include culturing an Aspergillus species on a suitable medium. Preferably, this medium is a solid surface medium. These methods further include extracting extracellular compounds from the medium with water, so that a liquid fermentation extract is obtained. These methods further include filtering the obtained fermentation extract to remove cell biomass and spores therefrom, thereby providing a liquid fermentation extract. Finally, the disclosed methods include refrigerating the liquid fermentation extract until the use thereof. Preferably, such refrigeration is done at about 4° C.

Preferably, the methods disclosed herein are used for the preparation of topical prophylactic and therapeutic compositions.

In yet further accordance with the teachings of the present invention, disclosed herein are methods for the prevention and treatment of viral-induced tumors in mammals. Use of these methods neither destroy healthy uninfected tissue, nor result in either significant systemic side effects, scarring, disfigurement or discomfort to the mammal treated therewith. Furthermore, use of these methods results in the destruction of latent viral DNA maintained in surrounding tissues, so that instances of incomplete resolution and frequent tumor recurrence are reduced. These methods include preparing a fermentation extract and/or a derivative thereof in a pharmaceutically-acceptable carrier, so that a prophylactic and/or therapeutic composition is provided for the prevention and/or treatment of viral-induced tumors in mammals. These methods further include administering a therapeutically-effective amount of the composition to a mammal in need thereof. Such administration may, in the case of a prophylactic treatment, be on that area of the mammal on which it is anticipated that such preventive treatment is needed or, in the case of a therapeutic treatment, be directly on the viral-induced tumor of the mammal in need thereof. Preferably, such application is a topically performed.

Preferably, providing the prophylactic and therapeutic compositions of the present invention includes preparing a fermentation extract, and in particular a fermentation extract of Aspergillus. More preferably, the method involves providing a fermentation extract of *Aspergillus niger*, with the providing of a fermentation extract of *Aspergillus niger* 1.2 AN29 or 1.2 AN39 being the most preferred of all.

If desired, the method may further include the preparation of a derivative of the fermentation extract.

In a particular aspect of the present invention disclosed herein are prophylactic and therapeutic topical compositions and methods for the use thereof for the prevention and treatment of Epstein-Barr Virus-induced tumors in mammals.

In a further particular aspect of the present invention, disclosed herein are prophylactic and therapeutic topical compositions and methods for the use thereof for the prevention and treatment of cottontail rabbit papillomavirus-induced tumors in mammals.

In still another particular aspect of the present invention, disclosed herein are prophylactic and therapeutic topical compositions and methods for the use thereof for the prevention and treatment of papillomavirus-induced tumors in mammals.

These and further objects and advantages of the present invention will become readily apparent upon a reading of the following invention in conjunction with the examples thereof.

DESCRIPTION OF PREFERRED EMBODIMENTS

The present invention includes prophylactic and therapeutic topical compositions for the prevention and treatment of viral-induced tumors in mammals. These compositions are prepared from fermentation extracts and/or derivatives thereof. These fermentation extracts and derivatives thereof may then be mixed with a pharmaceutically-acceptable carrier to manufacture the therapeutic compositions of the present invention.

By the term "fermentation extracts" what is referred to are extracts of the milieu, and in particular the fermentation milieu, which has been inoculated with a culture of a suitable microbe and in which the microbe has been cultured (grown).

By the terms "derivatives of" and "derived from" when used in reference to the fermentation extracts, what is meant are compositions or components, such as particular enzymes or combinations of enzymes, which have either been obtained (derived or isolated) from the fermentation extracts. By way of illustration, an example of such a derivative would be a fermentation extract which has been concentrated or filtered. The terms "derivatives of" and "derived from" are used equally to refer to compositions and compounds which are both identical to those compositions or components of the fermentation extract and which demonstrate the same prophylactic and therapeutic properties of the fermentation extracts. By way of illustration, such definition includes components of the fermentation extract itself (such as the active agent thereof) which have been isolated (and, if desired, purified) from the fermentation extract. By way of further illustration, such definition also includes compositions or compounds which have been constructed (i.e., synthetically constructed) to mimic the active agent(s) having the prophylactic and therapeutic properties of the fermentation extracts of the present invention.

More particularly, the fermentation extracts and derivatives thereof which are disclosed herein are water extracts of surface fermentations (or derivatives of such water extracts) which have been inoculated with a culture of a suitable microbe.

The fermentation extracts are, preferably Aspergillus fermentation extracts and, more particularly, an *Aspergillus niger* fermentation extracts. Most preferred are an *Aspergillus niger* 1.2 AN29 fermentation extracts and an *Aspergillus niger* 1.2 AN39 fermentation extracts.

In particular, it has been observed that water extracts of surface fermentations inoculated with an *Aspergillus niger* culture contributes to the prevention of and the disappearance of warts in mammals.

The pharmaceutically-acceptable carrier may be any such carrier well-known to those skilled in the art. It is preferred that such a carrier be a hydrophilic substance that aids the prophylactic and therapeutic compositions to penetrate the skin. Examples of such carriers include, but are not limited aqueous menthol solutions, water, propylene glycol, lanolin, butyl alcohol, absolute alcohol, isopropyl alcohol, dimethyl sulfoxide, ether ethyl lactate, aqueous solutions of menthol and mixtures thereof. Another example of such a carrier is the well-known "Vehicle N", a composition comprised of ethyl alcohol, isopropyl alcohol, purified water, Laureth-4 (a surfactant) and propylene glycol.

The precise amounts of the fermentation extract (and/or derivatives thereof) and the pharmaceutically-acceptable carrier, to employ in preparing the prophylactic and therapeutic compositions of the present invention are well within the skill of the art to determine. However, generally, a concentration of about 1% (w/v) to about 15% (w/v) of fermentation extract (or derivative thereof) is preferred with 8% (w/v) being especially preferred.

The prophylactic and therapeutic compositions may be formulated as desired for topical application on either the area of the mammal to be protected or on the afflicted tumor, such as a wart, of the mammal in need thereof. Such formulations include liquid compositions, such as oil-based ointments, linaments and tincture compositions. Creams, soaps and gels are especially preferred for their ability to keep the prophylactic and therapeutic compositions in prolonged contact with the skin and/or tumor for a sufficient period of time.

While not precisely understood, it is believed that the mode of action of the compositions of the present invention may not necessarily be directly antiviral or antitumor in nature. Rather, it is believed that is it possible that the mode of action of the compositions disclosed herein may be the result of a general stimulation of the immune system. Cell-mediated responses may be important for the AN-1 antigen which may induce a generalized immunological response which affects tumor growth. In this respect, we believe that the compositions of the present invention may be immunopotentiators. Indeed, previous studies have shown that a cell-mediated response is most likely responsible for regression of papillomavirus-induced for benign and pre-malignant neoplasia.

The prophylactic and therapeutic compositions of the present invention are useful for the prevention and treatment of viral-induced tumors, such as those resulting from humanpapilloma-viruses (HPV), cottontail rabbit papilloma virus (CRPV), equine papillomavirus (EPV) and Bovine papillomavirus (BPV).

The prophylactic and therapeutic compositions of the present invention are provided by, first, preparing a suitable growth medium. Preferred is a solid surface medium. The precise medium to utilize will vary according to the microbe to be cultured thereon, as is well within the skill of the art to ascertain. In the event that an Aspergillus is to be cultured thereon, it is preferred that the medium include: 7.9% (w/w) SOLKA FLOG BNB 100 (James River Corp., U.S.A.); 7.9% (w/w) oat hulls; 7.9% (w/w) peanut meal; 15.8% (w/w) beet pulp; 0.39% (w/w) $KH_2PO_4$; 13 ppm $ZnSO_4$; and 60% (w/w) water.

The medium is then sterilized, cooled and inoculated with spores of the precise Aspergillus species to be cultured thereon. After inoculation and mixing, the medium is transferred to porous metal trays at a depth of approximately 0.75 inches. These trays are then incubated in a high humidity environment at 30° C. to 32° C. for about 72 hours during which time the Aspergillus species is cultured. The contents are then harvested (extracted) by stirring in water (water extraction) for several hours, so that a liquid fermentation extract is obtained. The liquid fermentation extract is then subjected to a filtration (passed through a final filter) to remove cell biomass, spores and other insolubles from the extract.

If desired, the liquid filtered extract may then be used as such, or it may be further processed, such as by being concentrated, so that a suitable derivative thereof is provided.

If not to be used immediately, the liquid filtered extract (and/or derivative thereof) is, preferably, refrigerated at 4° C. until use.

If long-term storage is desired, the liquid filtered extract (or derivative thereof) may then be vacuum concentrated, followed by a clarifying filtration. The filtrate (or derivative thereof) may then be freeze-dried. The resulting freeze-dried powder of the fermentation extract (or derivative thereof) is very soluble in water. When use thereof is desired, the freeze-dried powder may be redissolved in a liquid, such as water, and/or in the pharmaceutically-acceptable carrier.

The prophylactic and therapeutic compositions of the present invention may be used in methods for the prevention and treatment of viral-induced tumors in mammals. These methods include administering a therapeutically-effective amount of the prophylactic and therapeutic compositions including an Aspergillus fermentation extract (or a derivative thereof) in a pharmaceutically-acceptable carrier to a mammal in need thereof.

By the term "therapeutically-effective amount" what is meant is an amount which is effective for either prophylactic or therapeutic purposes to prevent or mitigate the growth of new or existing viral-induced tumor(s) in question.

The precise amount of the prophylactic and therapeutic compositions to be applied is well within the skill of the art to determine. However, it is desired for the quantity of the topical prophylactic and therapeutic compositions of the present invention to be applied to the (afflicted) area of the skin (such as that area where the viral-induced tumor is located) of a mammal in need thereof, be that amount which is necessary to thinly saturate the said afflicted area.

The prophylactic and therapeutic compositions can be administered in any suitable manner well-known to those skilled in the art. Such methods can include subcutaneous or intravenous injection. Preferably, this administration is a topical administration, such as by being applied to the surface of the skin or tumor (or afflicted area in need thereof) with the aid of an eye-dropper, a porous applicator (such as a gauze, swab or cloth, a roll-top applicator) a brush or any other suitable application means, as desired.

If desired, the prophylactic and therapeutic compositions may be applied before infection in a prophylactic treatment to prevent initial infection. We have found that the prophylactic and therapeutic compositions have significant tumor reducing potential when applied either shortly after infection, or when applied to existing tumors. It is contemplated that such applications will be performed at least one to two times per day as long as the tumors persist. However, the precise frequency of these applications may be increased and/or decreased as desired or needed, as is well within the skill of the art to determine. Care should be taken to avoid the development of skin reactions to the compositions, but in any event, we have found that any such reactions eventually diminished without any harm to the specimen being tested.

Having thus described the prophylactic and therapeutic compositions of the present invention, as well as the method for the preparation thereof and the use thereof, the following Examples are now presented for the purposes of illustration only and are neither meant to be, nor should they be, read as being restrictive.

EXAMPLE 1

Preparation of an *Aspergillus niger* 1.2 AN39 Fermentation Extract

First, a suitable growth medium was prepared comprised of 7.9% (w/w) SOLKA FLOC BNB 100 (James River Corp., U.S.A.); 7.9% (w/w) oat hulls; 7.9% (w/w) peanut meal; 15.8% (w/w) beet pulp; 0.39% (w/w) $KH_2PO_4$; 13 ppm $ZnSO_4$; and 60% (w/w) water.

The medium was then sterilized, cooled and inoculated with spores of *Aspergillus niger* 1.2 AN39 which has been deposited under the provisions of the Budapest Treaty in the Agricultural Research Service Culture Collection (EL), 1815 N. University St., Peoria, Ill. (U.S.A.) on Jul. 30, 1993 under Accession Number 21126.

After inoculation and mixing, the medium was transferred to porous metal trays at a depth of approximately 0.75 inches. These trays were then incubated in a high humidity (water-saturated) environment at 30° C. to 32° C. for about 72 hours to produce the desired *Aspergillus niger* 1.2 AN39 cultures. The cultures were then harvested by stirring in water (water extraction) for several hours followed by filtration (passed through a final filter) to remove cell biomass, spores and other insolubles.

The filtrate was then vacuum concentrated, followed by a clarifying filtration. The resulting composition was an *Aspergillus niger* 1.2 AN39 fermentation extract which was designated "AN-1".

The liquid filtered extract was then refrigerated at 4° C. until use.

EXAMPLE 2

Preparation of an *Aspergillus niger* 1.2 AN29 Fermentation Extract

An *Aspergillus niger* 1.2 AN29 fermentation extract was prepared in the same manner as the *Aspergillus niger* 1.2 AN39 fermentation extract described above in Example 1, with the exception that the cooled, sterilized medium was inoculated with spores of *Aspergillus niger* 1.2 AN29 which has been deposited under the provisions of the Budapest Treaty) in the Agricultural Research Service Culture Collection (NRRL), 1815 N. University St., Peoria, Ill. (U.S.A.) on Sep. 7, 1993 under Accession Number 21139. This composition was designated "AN-2".

The liquid filtered extract was then refrigerated at 4° C. until use.

EXAMPLE 3

In Vitro Therapeutic Index of *A. niger* Fermentation Extract

An estimation of the efficacy of the enzyme composition of the present invention against Epstein-Barr virus, a herpestype virus, in vitro, was determined to ascertain the potential usefulness of the therapeutic composition of the present invention in vivo.

A standard estimation of the potency of antiviral agents is by a comparison of the ratio of the $ED_{50}$ obtained for cytotoxicity to the $ED_{50}$ obtained for viral inhibition. This relationship is referred to as the "in vitro therapeutic index" or "selectivity index". Relative to the instant matter, the selectivity index of antiviral agents must be more than 100 to indicate a useful effect on viral inhibition in animal experiments as described in (1).

The estimation made herein was performed by a superinfection of Raji cells with a EBV viral cell line commonly referred to as P3HR-1. P3HR-1 is a standard laboratory EBV strain. After superinfection, the cultures were assayed for early antigen production.

1. Preparation of Human Foreskin Fibroblast Cells

Newborn human foreskins were obtained as soon as possible after circumcisions were performed and placed in Dulbecco's Minimal Essential Medium (DMEM) (GIBCO BRL, Life Technologies, Inc., Gaithersburg, Md. U.S.A.) supplemented with (per ml DMEM) 50 µg vancomycin, 3 µg fungizone, 100 units penicillin and 25 µg gentamycin at 37° C. for 4 hours.

The medium was then removed, the foreskin minced into small pieces and repeatedly washed with Dulbecco's phosphate buffered saline (DPBS) (GIBCO BRL), from which the calcium and magnesium were omitted, until red cells were no longer visually present.

The tissue was then trypsinized using trypsin at 0.25% (w/v) with continuous stirring for 15 minutes at 37° C. in a $CO_2$ incubator. At the end of the 15 minute period, the tissue was allowed to settle to the bottom of the flask. The supernatant containing cells was then poured through a sterile cheesecloth and into a second flask containing DMEM and 10% (v/v) fetal bovine serum (Hyclone, USA). After each filtration of cells, the cheesecloth was washed with a small amount of DMEM-containing serum. Fresh trypsin was again added to the foreskin pieces as described above and the procedure was repeated until no more cells became available.

The second flask (containing the medium and the trypsinized cells) was kept on ice throughout the trypsinizing procedure.

The cell-containing medium in the second flask was then centrifuged at approximately 1000 RPM (about 100 g) at 4° C. for ten minutes (the minimum centrifugal force required to pellet the cells without causing damage thereto). The supernatant liquid was discarded and the cells resuspended in about 50 ml of DMEM with 10% (v/v) fetal bovine serum.

The cells were then placed in an appropriate number of 25 $cm^2$ tissue culture flasks. The cells were kept on 50 µg/ml DMEM vancomycin and 3 µg/ml DMEM fungizone at 37° C. for about 72 hours until the cells were subconfluent. The cells were then subcultured as described above, but in larger flasks and with fresh medium. This procedure was then repeated two more times until four passages were achieved.

2. Screening Assays for EBV

A. Virus

The prototype of infectious EBV used was the virus derived from supernatant fluids of the P3HR-1 cell line (obtained from the American Type Culture Collection (ATCC), Rockville, Md. (U.S.A.) under Accession Number VR603) following the procedure described in (12). This cell line produces nontransforming virus that causes the production of early antigen (EA) after primary infection or superinfection of B cell lines.

B. Cell Lines

Raji (obtained from the American Type Culture Collection (ATCC), Rockville, Md. (U.S.A.) under Accession Number CCL86) is a Burkitt's lymophoma cell line containing 60 EBV genomes/cell and was the primary cell used for screening antiviral activity against EBV early antigen (EA) expression.

All viral cell lines (the P3HR-1 as well as the Raji viral cell lines) were maintained in RPMI-1640 medium (GIBCO BRL) supplemented by 10% (v/v) fetal bovine serum, 2.05 mM/ml medium L-glutamine and 25 µg/ml medium gentamycin. Twice weekly half of the medium volume was replaced with fresh medium and the cell concentration adjusted to $3 \times 10^5$/ml as described by (12). The cells were then maintained at 37° C. in an humidified (90%) atmosphere with 5% (v/v) $CO_2$ until used.

3. Immunofluorescence Assays with Monoclonal Antibodies

The Raji cells were infected as described by (12) with the P3HR-1 strain of EBV. The composition, obtained as described above in Example 1, was then added after passive adsorption for 45 minutes at 37° C. and washing of the cell cultures with Dulbecco's phosphate buffered saline (DPBS) but without calcium and magnesium. The cultures were then incubated at 37° C. for two days in RPMI-1640 medium (described above) to allow viral gene expression. Following the 48 hour incubation period, the number of cells of each sample were counted with a hemacytometer as described in (12) and then spotted onto wells of Toxoplasmosis slides (Bellco Glass Co., U.S.A.) and air-dried.

Monoclonal antibodies (graciously provided by Dr. Gary Pearson, Georgetown University, U.S.A.) to the diffuse early antigen EA(D) (DuPont, U.S.A.) was then added to the Raji cells in the wells in the slides as described in (12). This was followed by the addition of a fluorescein conjugated goat anti-mouse IgG antibody (Fisher Scientific, U.S.A.), following the procedure described in (12) and the number of fluorescence positive cells in the wells of the slides were visually counted using a fluorescense microscope. The total number of cells in the cultures positive for EA(D) were then calculated and compared as described by (12), the early antigen expression of the EBV being inhibited in those Raji cells that did not exhibit fluorescence.

4. In Vitro Cytotoxicity

In vitro cytotoxicity of AN-1 was determined in human foreskin fibroblast (HFF) cells, obtained as described above, following the technique and under the conditions described by (13) modified as follows: twenty-four hours prior to assay, low passage HFF cells were plated into 96-well tissue culture plates (having 8×12 flat-bottom wells) (Becton Dickinson Labware, U.S.A.) a concentration of $2.5 \times 10^4$ cells per well. The cells were in 0.1 ml of DMEM containing 10% (v/v) fetal bovine serum (Hyclone, USA). The cells were then incubated for twenty-four hours at 37° C. in a $CO_2$ incubator. The medium was then aspirated and 100 µl of DMEM containing 2% (v/v) of fetal bovine serum was added to all but the eight wells in the first row. 125 microliters of AN-1 was the added to each respective well in the first row and the AN-1 was then diluted serially 1:5 (giving an AN-1 concentration range in the wells of from 100 µg/ml to 0.03 µg/ml) throughout the remaining wells by transferring 25 µl using the Cetus Liquid Handling Machine (Perkin-Elmer Corp., U.S.A.). The plates were then incubated for seven days in a $CO_2$ incubator at 37° C. Then, the cell-free medium containing AN-1 solution was aspirated and 200 µl/well of 0.01% (v/v) neutral red in Dulbecco's Phosphate Buffered Solution was added. This was incubated at 37° C. in a $CO_2$ incubator for one hour. The dye was then aspirated and the cells were washed using a Nunc Plate Washer (Nunc, Inc., U.S.A.). After removing the DPBS wash, 200 µl/well of 50% (v/v) EtOH/1% (v/v) glacial acetic acid (in $H_2O$) was added. The contents were mixed by rotating the plates on an orbital shaker for 15 minutes. Then, the optical density of each well was read at 550 nm with a plate reader (Beckman Instruments Inc., U.S.A.).

Visual inspection of the HFF cells in each assay system (generally stationary cells), which were treated with 100 µg/ml of AN-1, indicated no toxicity.

Also, the cytotoxicity of AN-1 has been determined in the HFF cell proliferation assay (rapidly-growing HFF cells). The cell proliferation assay of AN-1 for rapidly-growing human foreskin fibroblast cells was done. Twenty-four hours prior to assay, HFF cells (obtained as described above) were seeded in six-well tissue culture plates (having 2×3 flat bottom wells) (Becton Dickinson Labware, U.S.A.) at a concentration of $2.5 \times 10^4$ cells per well in DMEM containing 10% (v/v) fetal bovine serum. On the day of the assay, AN-1 was diluted serially in DMEM containing 10% (v/v) fetal bovine serum at increments of 1:5 giving an AN-1 concentration in each of the various wells covering a range of from 100 µg/ml to 0.03 µg/ml. The medium from the cells was then aspirated and 2 ml of AN-1 concentration was then added to each well. The cells were then incubated in a $CO_2$ incubator at 37° C. for seventy-two hours. Then, the cell-free medium containing AN-1 in solution was removed and the cells (monolayer) washed with DPBS that contained neither calcium nor magnesium. The DPBS was then removed by aspiration. One ml of 0.25% (w/v) trypsin was added to each well and incubated until the cells started to become separated from the bottom of the wells of the plate. The cell-medium mixture was then pipetted up and down vigorously to break up the cell suspension and 0.2 ml of the mixture was added to 9.8 ml of the diluent ISOTON III (Coulter Electronics Inc., U.S.A.) and the cells counted using a Coulter Counter (Coulter Electronics Inc., U.S.A.). Each sample was then counted three times with three replicate wells per sample.

There was no toxicity of AN-1 at the 100 µg/ml level with this more stringent assay for toxicity.

Also, AN-1 was not toxic to the untransfected (EBV-free) Raji Burkitt's Lymphoma cell line at the 100 µg/ml level ($IC_{50}$ being greater than 100 µg). The method that was used for the toxicity assay of AN-1 for untransfected (EBV-free) Raji Burkitt's Lymphoma cells was described by (12) at page 85.

5. Results

The results of these screenings are given below, wherein: $EC_{50}$ (50% effective concentration) is the concentration required to inhibit viral cytopathogenicity by 50%; $IC_{50}$ (50% inhibitory concentration) is the concentration required to inhibit cell proliferation by 50%; and S.I. stands for "Selective Index". The $SI=IC_{50}/EC_{50}$. (1).

When the antiviral activity of AN-1 to early antigen (EA) expression of Epstein-Barr virus (EBV) in RAJI cells (~60 EBV copies/cell) was tested, the selectivity index (SI) obtained was greater than 137 ($IC_{50}>100$ µg/ml+$EC_{50}$0.73 µg/ml), as follows: EBV (RAJI Cells)

Immunofluoresence—MCG/ml EC $_{50}$=0.73; $IC_{50}>100$; SI>137

Since the SI of AN-1 was more than 100 (>137) in RAJI cells, a useful effect on viral inhibition in mammal experiments is indicated.

The $EC_{50}$ for acyclovir (an antiviral standard which has inhibitory activity towards several herpes viruses) was 4.9 µg (ACV $EC_{50}$4.9). Thus, the crude AN-1 sample was 6.71 times more potent than acyclovir. It is anticipated that, after it is purified, the specific activity of the AN-1 composition would be increased.

[Acyclovir is 2-Amino-1,9-dihydro-9-[(2-hydroxyethoxy)methyl]-6H- purin-6-one; acycloguanosine; 9-[(2- hydroxyethoxy)methyl]guanine. $C_8H_{11}N_5O_3$; Molecular Weight of 225.21. It is an orally active acyclic nucleoside with inhibitory activity towards several herpes viruses. The preparation of acyclovir is described in U.S. Pat. No. 4,199,574.]

The crude preparation of antiviral agent AN-1 did not inhibit either herpes simplex virus type 1, herpes simplex virus type 2, human cytomegalovirus or varicella zoster virus in vitro at the 100 µg/ml level.

EXAMPLE 4

Use of *A. niger* Fermentation Extract as a Topical Therapeutic Agent

An excellent animal model system for the in vivo study of humanpapilloma virus related diseases can be found in rabbits using the NIH (National Institutes of Health) cottontail rabbit papillomavirus (CRPV) rabbit model system. This system has been used previously for the testing of putative viral agents.

CRPV is naturally endemic in Midwestern cottontail rabbits, producing cutaneous papillomas in which about 25% of these lesions progress to invasive carcinomas. Inoculating CRPV onto the skin of domestic rabbits consistently produces warts. Thus, the CRPV rabbit model system can be used to test the efficacy of various antiviral agents for their ability to prevent or mitigate wart growth.

A controlled study of the therapeutic effects of the crude cell-free fermentation extract (AN-1), obtained as described above in Example 1, was performed in the NIH CRPV-rabbit model system. In the first stage of this study the presence and size of the tumors were compared in animals which had either: a) received topical treatments with only 50% glycerol (Group 1); or b) received 8% AN-1 in 50% glycerol (Group 2); or c) received no treatment at all until nine weeks following infection with CRPV and then treatment with 8% AN-1 in 50% glycerol. In this fashion, both the prophylactic as well as the therapeutic properties of the compositions of the present invention could be studied by reference to the Group 2 (for prophylactic properties) and Group 3 (for therapeutic properties) in comparison to the Group 1 and the control group.

METHODS AND TECHNIQUES

1. Preparation of the Virus

CRPV was isolated from the tumors of wild rabbits and prepared by standard methods described in (2) which produced a 10% (w/v) homogenate of cottontail rabbit warts cleared of cellular debris. The virus was titred by serial dilution and scarification on domestic female Dutch Belt Rabbits, as described in (3), thereby producing warts in about 3 to 4 weeks. A portion of this virus was then purified by isopycnic CsCl density gradients, as described in (4) giving the purified virion.

The excised tumors were then frozen in liquid nitrogen, pulverized in a mortar and pestle and a 10% (w/v) suspension prepared as described by (4). The viral supernatant was then applied to a velocity step gradient of CsCl at 43 g/100 ml, 32 g/100 ml and 27 g/100 ml and subjected to centrifugation at 70,000 g (in an SW27 rotor) for two hours at 18° C., as was described by (2). The viral band was then collected, dialyzed for 48 hours, diluted and made to a density of 1.34 g/ml with CsCl as was also described by (2). The virus was then banded in a SW 50.1 rotor at 100,000 g for 40 hours at 18° C., collected and dialyzed, as was further described by (2).

2. Experimental Protocol

Two rabbits (C 1 and C 2) were immunized with purified CRPV virions (obtained as described above) as described in (2).

Three groups of seven rabbits each were infected with CRPV obtained as described above. The back of each rabbit was infected at eight sites (four sites on the left-hand side and four sites on the right-hand side) with 50 µl of a 1:4 dilution of the stock virus (approximately $32 \times ID_{50}$ units). Such infection was performed by scarification, as described in (3).

One week later, topical treatments began. The specimens of Group 1 (the control group) were given twice daily treatments with 100 µl of 50% (v/v) glycerol in deionized water. The specimens of Group 2 were given twice daily treatments with 100 µl 8% (w/v) AN-1 in 50% (v/v) glycerol in deionized water. The specimens of Group 3 were given twice daily treatments with 100 µl of the same composition as was given to the specimens of Group 2, but such treatment were not started until the start of the ninth week after infection, at which time most of the infection sites had already developed tumors. Treatment was continued for two months for each group.

Treatments were effectuated by contacting the infected tumor sites with the particular treatment and maintaining such contact for approximately five (5) seconds with a "rubber policeman" to let the treatments work-in.

3. Isolation of Cellular DNA

Tumor tissues from each of the specimens of the three groups of section 2 were extracted, minced and treated (digested) with proteinase, as is described by (5). Potassium chloride and the ethanol were then added to the cooled digest to precipitate, respectively, the protein complexes therein and the total cellular nucleic acids therein as is described by (5). RNA was then removed by treatment with ribonuclease A followed by sodium dodecyl sulfate-proteinase digestion, phenol-chloroform extractions and ethanol precipitations, as was also described by (5).

4. Preparation of Radiolabeled CRPV DNA

CRPV DNA was then obtained from the DNA isolated as described above in section 3 and molecularly cloned into pBR322 (Clontech Laboratories, U.S.A.) as described in (2). The cloned CRPV DNA was then excised from its plasmid vector by treatment with EcoRI followed by agarose gel electrophoresis and electro-elution of the appropriate DNA band as described in (2). This CRPV DNA was then radiolabeled with $^{32}$P-dCTP by nick translation as described in (6). Specific activities of about $3 \times 10^8$ cpm/µg were customarily achieved.

5. DNA Analysis

DNA filter hybridizations were performed under stringent conditions as described by (5). Cellular DNA was extracted as described in (5) from the DNA isolated as described above in section 3 with protease and detergent, phenol and chloroform, and subsequently analyzed by the polymerase chain reaction (PCR) using GeneAmp (TM) (Perkin-Elmer, U.S.A.) and oligomer primers derived from the CPRV E6 open reading frame. The sequences used for the primers were:

5'-GAACTGCCTGCCACGCTCGC-3'(SEQ ID NO: 1)
5'-CGCCTGGCCCTAGGTCAAC-3'(SEQ ID NO: 2)

After 35 cycles, amplification of 0.5 µg of cellular DNA followed by hybridization to a radiolabeled CRPV DNA probe could detect less than 1 fg of CRPV DNA in the original samples. See (3).

6. Serological Assays

Peripheral blood was drawn from each of the specimens of section 2 for enzyme-linked immunoabsorbent assay (ELISA) tests for humoral antibody to CRPV virion proteins. Purified virions described above in section 1 of this example were used in combination with Freund's complete and incomplete adjuvants to produce anti-CRPV sera as described in (7). Using 10 ng of purified virion proteins in standard ELISA assays as described in (7), these sera were found to have titres of $7.7 \times 10^4$ to $4.7 \times 10^5$. These sera served as positive controls in ELISA assays [as described in (7)] for the detection of humoral CRPV antibodies in experimental animals. Serum reactivity to the *Aspergillus niger* fermentation extract (AN-1) was determined using 1 mg of the lyophilized powder (obtained as described above in Example 1) as the antigen. In both sets of assays, sera from rabbits both pre-infection and from the termination of the study were analyzed. Comparisons in which the titre increased by a factor of at least 4 were considered significant.

7. Statistical Analysis

The significance of the presence or absence of warts in the individual sample groups compared to the control groups was measured by a chi-square test described in (8). Differences in positivity of serum antibody response were assessed using a Fisher Exact Test as described in (9), (10) and (11). "p values" were calculated in the manner described in (9)–(11) using the Fisher Exact Test. As used herein, p values refer to probability values. Probability values (p) of 0.05 or less are considered significant, indicating that there is less than a 5% chance that such a result occurred randomly.

8. Results

A. Clinical Observations

The results of the clinical observations hereafter discussed are summarized in Table 1, as follows:

TABLE 1

Clinical Observations of Effects of Topically Applied *A. niger* Fermentation Extract on Growth and Removal of Warts by CRPV Infection Sites W/Tumors

| Group | Treatment | # of Specimens | # of Sites | After 56 Days No. | 56 Days Percent | After 112 Days No. | 112 Days Percent |
|---|---|---|---|---|---|---|---|
| 1 | Control | 7 | 56 | 54 | 96 | 42 | 75 |
| 2 | 7 days post Infection | 7 | 56 | 45 | 80 | 24 | 43 |
| 3 | 56 days post Infection | 7 | 56 | 53 | 94 | 32 | 57 |

Eight weeks after the beginning of treatment, tumors were observed in 96% of the infection sites of animals in Group 1 (which received none of the composition) and in 94% of the animals in Group 3 (p<0.01), who had not yet received any treatment whatsoever. In comparison therewith, tumors were observed in only 80% of the animals in Group 2. Group 2 was the group who had received prophylactic treatments with the composition and the only specimens who, until this time, had received any of the composition. Thus, it can be seen that when applied topically for an extended period beginning within one week of infection by CRPV, there was a 17% reduction in the number of tumors observed when compared to controls after eight weeks. An additional nine weeks later (without further treatment) the specimens demonstrated a 43% reduction in the number of tumors observed when compared to controls.

These 17% and 43% reductions in tumors demonstrate the prophylactic properties of the composition of the present invention.

Relative to the specimens of Group 3 (the Group who had received the therapeutic treatments with the composition), it was found that when AN-1 was repeatedly topically applied to specimens having existing tumors (present nine weeks after CRPV infection), after about eight weeks, such specimens experienced 24% fewer tumors than control specimens (the percentage of infection sites with tumors for specimens of Group 3 was 57% with a p>0.05). This 24% reduction in tumors demonstrates the therapeutic properties of the composition of the present invention.

In summary then, this study demonstrates both the prophylactic and therapeutic properties of the compositions of the present invention for the prevention and treatment of viral-induced tumors.

1. Skin Reactions

It is noted here that several of the specimens in each Group developed "rashes" (red, lumpy area) after a few weeks of AN-1 administration which were initially only in the vicinity of the drug administration. However, as the experiment progressed, we found rashes to be more widely spread.

The skin rashes observed are reminiscent of red skin and itchiness which is observed in regressing warts in patients.

It is suspected that the specimens were experiencing delayed allergic responses as a result of previous or extended exposure to *Aspergillus niger* antigens. Delayed hypersensitivity, such as was observed, is a cellular immune response. Necropsy of animals revealed no untoward side effects on major organs. In some of the tumor sites on AN-1 treated animals, superficial dermas were infiltrated with moderate numbers of lymphocytes and small numbers of macrophages and plasma cells. Similar infiltrates were found in the non-papillomavirus nodules associated with the hypersensitivity response.

2. Wart Regression 112 days after infection, all groups showed some tumor regression. At this time, the percentage of infection sites with tumors for Group 1 was 75%. Therefor, there was a 25% tumors regression. There was an additional 24% wart regression in tumors in the specimens of Group 3 due to treatment with the fermentation extract. However, some of the tumors in Group 3 which had regressed were tumors which were in the process of regression prior to treatment with AN-1, as determined by intermediate tumor size measurements.

B. Serological Observations

Serological studies testing reactivity to CRPV and AN-1 antigens by ELISA assays of both pre and post-study sera from all specimens is shown in Table 2. C 1 and C 2 stand for, respectively, Control Specimen #1 and Control Specimen #2, which served as controls for this ELISA assay:

TABLE 2

ELISA Assay Results Using CRPV and AN-1 Antigens Titre of Sera From Each Animal

| Spec. | Pre-Sera AN-1 Ag | Post-Sera AN-1 Ag | Ratio Post/Pre | Pre-Sera CRPV Ag | Post-Sera CRPV Ag | Ratio Post/Pre | # of Tumors |
|---|---|---|---|---|---|---|---|
| Group 1 (Control Group) | | | | | | | |
| 1 | 160 | 160 | 1 | 320 | 320 | 1 | 8 |
| 2 | 10 | 10 | 1 | 320 | 40 | −1 | 8 |
| 3 | 10 | 40 | 4 | 10 | 40 | 4 | 7 |
| 4 | 20 | 40 | 2 | 160 | 320 | 2 | 8 |
| 5 | 20 | 20 | 1 | 20 | 40 | 2 | 0 |
| 6 | 10 | 10 | 1 | 10 | 10 | 1 | 8 |

TABLE 2-continued

ELISA Assay Results Using CRPV and AN-1 Antigens
Titre of Sera From Each Animal

| Spec. | Pre-Sera AN-1 Ag | Post-Sera AN-1 Ag | Ratio Post/Pre | Pre-Sera CRPV Ag | Post-Sera CRPV Ag | Ratio Post/Pre | # of Tumors |
|---|---|---|---|---|---|---|---|
| 7 | 20 | 20 | 1 | 10 | 20 | 2 | 3 |
| Group 2 | | | | | | | |
| 8 | 10 | 20 | 2 | 10 | 10 | 1 | 8 |
| 9 | 10 | 10 | 1 | 10 | 10 | 1 | 8 |
| 10 | 10 | 10 | 1 | 10 | 10 | 1 | 0 |
| 11 | 20 | 160 | 8 | 20 | 160 | 8 | 0 |
| 12 | 10 | 10 | 1 | 10 | 10 | 1 | 0 |
| 13 | 10 | 20 | 2 | 10 | 20 | 2 | 8 |
| 14 | 40 | 40 | 1 | 40 | 40 | 1 | 0 |
| Group 3 | | | | | | | |
| 15 | 160 | 640 | 4 | 160 | 640 | 4 | 3 |
| 16 | 320 | 320 | 1 | 320 | 160 | ~1 | 8 |
| 17 | 80 | 1280 | 16 | 80 | 640 | 8 | 2 |
| 18 | 40 | 40 | 1 | 40 | 160 | 4 | 8 |
| 19 | 40 | 40 | 1 | 20 | 20 | 1 | 0 |
| 20 | 10 | 40 | 4 | 10 | 80 | 8 | 8 |
| 21 | 160 | 640 | 4 | 20 | 160 | 8 | 3 |
| C1 | 320 | 360 | ~1 | 320 | 77760 | 243 | Immunized |
| C2 | 2560 | 2160 | ~1 | 640 | 466560 | 729 | Immunized |

Sera were diluted 1:10 and then two-fold dilutions thereafter. Positive control sera was diluted 1:10 and six-fold dilutions thereafter. Titre is inverse of dilution. End points are the last dilution with an Absorbance at 490 nanometers of 0.1 or greater. Increases of four-fold or more are considered significant. Controls consisted of specimens which had been immunized with the purified CRPV virions as described above (3).

The results seen above relative to Table 2 show that five (5) animals in Group 3 had a significant sero-positive response (a ratio of post to pre of four or more) to CRPV antigens, as opposed to only one (1) specimen in Group 1. This difference in the responses to CRPV antigens between the specimens of Group 1 (which received none of the composition of the present invention) and the specimens of Group 3 (which received a therapeutic treatment of the composition of the present invention) was significant by the Fisher Exact Test (p=0.05).

It is also noted that four specimens in Group 3 had a sero-positive response to AN-1 antigen, as compared with only one specimen in Group 1. While this is felt to be further indicative of the efficacy of the composition of the present invention, statistically, such a ratio is not significantly different from the response in Group 1 control animals.

While it is noted that the elevated antigen responses did not correlate with the observed tumor growth or lack thereof, generally an increase in response to one antigen paralleled an increase in response to the other in Groups 2 and 3. The role of this serological response to wart regression is not clear. These results would suggest a generalized hypersensitivity, as observed by the skin reactions, as the pathway by which AN-1 enhanced regression of papillomas.

C. Molecular Observations

PCR-hybridizations analyses as described in (3) were performed of the tumor negative sites in the specimens of the three groups in the current study to detect the presence of CRPV in virtually every CRPV-induced tumor. The investigation showed the presence of CRPV DNA in as many as 23% (3 of 13) of the tested sites in Group 1 as compared to only 6.5% (2 of 31) of the tested sites in Group 2 and 9.5% (2 of 21) of the tested sites in. Group 3 (see Table 3). In contrast, CRPV DNA was found in 76% of a sampling of tumors used as positive controls.

TABLE 3

Results of PCR DNA Analyses

| Group: | 1 | | 2 | | 3 | |
|---|---|---|---|---|---|---|
| Tumor1: | + | − | + | + | + | − |
| Total Positive2: | 4/5 (80%) | 3/13 (23%) | 2/4 (50%) | 2/31 (6.5%) | 7/8 (88%) | 2/21 (9.5%) |
| Results3: | 1:01 | 5:01 | 8:01 | 10:01 | 15:02+ | 15:05 |
| | 3:08+ | 5:02 | 8:02+ | 10:02 | 16:01+ | 15:06 |
| | 7:01+ | 5:03 | 9:01+ | 10:03 | 17:01+ | 15:07+ |
| | 7:02+ | 5:04+ | 13:01 | 10:04+ | 17:08+ | 15:08+ |
| | 7:03+ | 5:05+ | | 10:05 | 18:01+ | 17:03 |
| | | 5:06 | | 10:06 | 18:04+ | 17:05 |
| | | 5:07 | | 10:07+ | 20:01+ | 17:06 |
| | | 5:08 | | 10:08 | 21:06 | 17:07 |
| | | 7:04 | | 11:01 | | 19:01 |
| | | 7:05+ | | 11:02 | | 19:02 |
| | | 7:06 | | 11:03 | | 19:03 |
| | | 7:07 | | 11:04 | | 19:04 |
| | | 7:08 | | 11:05 | | 19:05 |
| | | | | 11:06 | | 19:06 |
| | | | | 11:07 | | 19:07 |
| | | | | 11:08 | | 19:08 |
| | | | | 12:01 | | 21:01 |
| | | | | 12:02 | | 21:02 |
| | | | | 12:03 | | 21:04 |
| | | | | 12:04 | | 21:05 |
| | | | | 12:05 | | |
| | | | | 12:06 | | |
| | | | | 12:07 | | |
| | | | | 14:01 | | |
| | | | | 14:02 | | |
| | | | | 14:03 | | |
| | | | | 14:04 | | |
| | | | | 14:05 | | |
| | | | | 14:06 | | |
| | | | | 14:07 | | |
| | | | | 14:08 | | |

[1]Infection sites were extracted for total DNA, amplified by PCR for the presence of CRPV DNA and analyzed by Southern Blot Analysis as described by (3). All tumor negative sites were examined in each of the three study groups. only a representative sampling of tumor positive sites were examined from each group.
[2]Number CRPV DNA positive over number tested (%). This is a summary of the raw data presented in this Table.
[3]Raw Data as follows:
Rabbit Number: Infection Site CRPV DNA Positivity. These results in the rabbit model system would seem to indicate the efficacy of the composition in for prophylactic and therapeutic purposes in humans as well as other mammals.

EXAMPLE 5

Use of *A. niger* Fermentation Extract as a Topical Therapeutic Agent

Two horses, each with wart-type tumors on their noses were treated for a two week period. The composition, obtained as described above in Example 1, was topically applied with a cotton gauze to the warts on one side of each of the horse's noses. As a control, sterile phosphate buffered saline (PBS) was topically applied with a cotton gauze to the warts on the other opposite side of each of the horse's noses.

1. Protocol

Treatments were conducted by placing 30 ml of solution onto several layers of gauze and dabbing it onto the warts until soaked. This was repeated twice during each treatment, so that the afflicted area was soaked. Treatments were made on days 0, 1, 2, 3, 7 and 14. Observations were made on days 0, 1, 2, 3, 7, 14, 21 and 30.

2. Results

By approximately 7 days, post-initiation of treatments of warts on the half of the muzzle being treated with the composition began changing in appearance (they appeared whiter, whereas others had a pink appearance).

By day 21, it was noted that the warts on the PBS half were much larger and it appeared as if they had grown in numbers. These warts appeared pink and quite viable. The warts on the composition-treated side were still present, however, they did not appear to have grown in either size or number. Again, they appeared white and quite crusty.

By 30 days, there appeared to be no change from 21 days.

3. Conclusions

The composition of the present invention exhibited a therapeutic effect on warts. The PBS-treated warts grew larger and spread, indicating that the warts were young at initiation of both treatments. Therefor, the difference in appearance between PBS-treated and the composition treated warts at 30 days is significant.

Many modifications may be made without departing from the basic spirit of the present invention. Accordingly, it will be appreciated by those skilled in the art that within the scope of the appended claims, the invention may be practiced other than has been specifically described herein.

Bibliography (1) Takeshima, H., Antiviral Agents. In The Search for Bioactive Compounds from Microorganisms, Omura, S., ed., Springer-Verlag, New York, N.Y. (1992) at page 50.

(2) Watts, S., et al., (1983) Virology 125 at 127–138.

(3) Ostrow, R., et al., (1992) Antiviral Res. 17 at 99–113.

(4) Ostrow, R., et al., (1982) Proc. Natl. Sci. USA 79 at 1634–1638.

(5) Manias, D., et al., (1989) Cancer Res. 49 at 2514–2519.

(6) Ostrow, R., et al., (1981) Virology, 108 at 21–27

(7) Poindexter, N., and Schlievert, P., (1985) J. of Infect. Dis. 151 at 65–72.

(8) Dowdy, S., and Wearden, S., Chi-Square Distributions In: Statistics for Research, J. Wiley & Sons, Inc., New York, N.Y. (1983) at 74–124.

(9) Latscha, R., (1955) Biometrika 40 at 74–86.

(10) Finney, D. J., (1948) Biometrika 35 at 145–156.

(11) Fisher, R. A. Statistical Methods for Research Workers, 14th ed., Hafner, New York, N.Y. (1973).

(12) Lidin, B., et al., (1992) Antiviral Res. 17 at 79–89.

(13) Korba, B. E. and J. L. Gerin (1992) Antiviral Res. 19, 55–70.

---

---

What is claimed is:

1. A prophylactic and therapeutic composition for the prevention and treatment of viral-induced tumors in mammals, comprised of an Aspergillus fermentation extract or a derivative thereof in a pharmaceutically-acceptable carrier, wherein the Aspergillus fermentation extract or derivative thereof is a fermentation extract or derivative thereof of *Aspergillus niger* strain NRRL Accession No. 21139 or *Aspergillus niger* strain NRRL Accession No. 21126.

2. A fermentation extract of *Aspergillus niger* strain NRRL Accession No. 21139 and derivatives of the extract.

3. A fermentation extract of *Aspergillus niger* strain NRRL Accession No. 21126 and derivatives of the extract.

* * * * *